US010016481B2

(12) United States Patent
Katoh et al.

(10) Patent No.: US 10,016,481 B2
(45) Date of Patent: Jul. 10, 2018

(54) SENSATION-IMPROVING AGENT

(71) Applicant: MEGMILK SNOW BRAND CO., LTD., Hokkaido (JP)

(72) Inventors: Ken Katoh, Saitama (JP); Hiroshi Ueno, Saitama (JP); Yuko Ono, Tokyo (JP); Noriko Ueda, Saitama (JP); Toshiya Kobayashi, Tochigi (JP); Takahiro Moriya, Miyagi (JP); Yutaro Obara, Yamagata (JP)

(73) Assignee: MEGMILK SNOW BRAND CO., LTD., Hokkaido (JP)

( * ) Notice: Subject to any disclaimer, the term of this patent is extended or adjusted under 35 U.S.C. 154(b) by 0 days.

(21) Appl. No.: 14/873,622

(22) Filed: Oct. 2, 2015

(65) Prior Publication Data

US 2016/0022771 A1    Jan. 28, 2016

Related U.S. Application Data

(62) Division of application No. 14/349,456, filed as application No. PCT/JP2012/075544 on Oct. 2, 2012.

(30) Foreign Application Priority Data

Oct. 4, 2011    (JP) .................................. 2011-220444

(51) Int. Cl.
| | |
|---|---|
| *A61K 38/17* | (2006.01) |
| *A61K 8/64* | (2006.01) |
| *A61K 8/66* | (2006.01) |
| *A61K 38/44* | (2006.01) |
| *C07K 14/47* | (2006.01) |
| *C12N 9/08* | (2006.01) |
| *C12N 9/22* | (2006.01) |
| *A61Q 19/00* | (2006.01) |
| *A23J 3/34* | (2006.01) |
| *A61K 38/40* | (2006.01) |
| *A61K 35/20* | (2006.01) |
| *A61K 8/98* | (2006.01) |
| *A61K 38/01* | (2006.01) |
| *A23L 2/66* | (2006.01) |
| *A61K 38/47* | (2006.01) |
| *A23K 10/12* | (2016.01) |
| *A23K 10/28* | (2016.01) |
| *A23K 20/147* | (2016.01) |
| *A23K 20/142* | (2016.01) |
| *A23K 50/40* | (2016.01) |
| *A23L 29/281* | (2016.01) |
| *A23L 33/18* | (2016.01) |
| *A23L 33/19* | (2016.01) |

(52) U.S. Cl.
CPC ........... *A61K 38/1709* (2013.01); *A23J 3/343* (2013.01); *A23K 10/12* (2016.05); *A23K 10/28* (2016.05); *A23K 20/142* (2016.05); *A23K 20/147* (2016.05); *A23K 50/40* (2016.05); *A23L 2/66* (2013.01); *A23L 29/281* (2016.08); *A23L 33/18* (2016.08); *A23L 33/19* (2016.08); *A61K 8/64* (2013.01); *A61K 8/66* (2013.01); *A61K 8/986* (2013.01); *A61K 35/20* (2013.01); *A61K 38/018* (2013.01); *A61K 38/40* (2013.01); *A61K 38/44* (2013.01); *A61K 38/47* (2013.01); *A61Q 19/00* (2013.01); *C07K 14/47* (2013.01); *C12N 9/0065* (2013.01); *C12N 9/22* (2013.01); *A23V 2002/00* (2013.01); *A61K 2800/40* (2013.01); *C12Y 111/01007* (2013.01); *C12Y 301/27* (2013.01); *Y02P 60/875* (2015.11)

(58) Field of Classification Search
None
See application file for complete search history.

(56) References Cited

U.S. PATENT DOCUMENTS

| | | | |
|---|---|---|---|
| 5,456,924 | A | 10/1995 | Bounous et al. |
| 6,607,743 | B1 | 8/2003 | Takada et al. |
| 2002/0123460 | A1 | 9/2002 | Kung et al. |
| 2003/0013661 | A1 | 1/2003 | Takada et al. |

(Continued)

FOREIGN PATENT DOCUMENTS

| | | |
|---|---|---|
| EP | 1 040 833 | 10/2000 |
| EP | 2 221 057 | 8/2010 |

(Continued)

OTHER PUBLICATIONS

Taiwanese Office Action issued in TW Patent Application No. 101136546, dated Dec. 9, 2016.
Naoya Sato et al., "Sen' iga Saibo karano NFG Sansei Sokushin Sayo o Shimeso Gyunyu Yurai Seibun no Sayo Kiko ni Kansuru Kenkyu", Abstract of 132nd Annual Meeting of Pharmaceutical Society of Japan, 29P1-am149, pp. 181, Mar. 5, 2012.
U.S. Appl. No. 13/981,698, which is the National Stage of PCT/JP2012/050617, filed Jan. 13, 2012.

(Continued)

*Primary Examiner* — Paul J Holland
(74) *Attorney, Agent, or Firm* — Greenblum & Bernstein, P.L.C.

(57) ABSTRACT

An object of the present invention is to provide a safety sensation-improving agent that can improve dulled peripheral sensations through daily ingestion or application to the skin. Another object of the present invention is to provide a sensation-improving food, beverage, feed, or cosmetics that can improve dulled peripheral sensations through oral ingestion or application to the skin. A sensation-improving agent containing a milk-derived protein and/or a hydrolysate therefrom as an active ingredient is provided. The milk-derived protein and/or the hydrolysate therefrom can be orally ingested or applied direct to the skin to improve dulled sensations, particularly peripheral sensations, and be formed into a sensation-improving food, beverage, feed, or cosmetics.

19 Claims, No Drawings

(56) References Cited

U.S. PATENT DOCUMENTS

| | | |
|---|---|---|
| 2003/0147830 A1 | 8/2003 | Phillips et al. |
| 2003/0206963 A1 | 11/2003 | Takada et al. |
| 2005/0176123 A1 | 8/2005 | Katunuma |
| 2006/0228345 A1* | 10/2006 | Motouri ............... A61K 38/44 424/94.4 |
| 2011/0124606 A1 | 5/2011 | Watanabe et al. |
| 2011/0151016 A1 | 6/2011 | McDonagh et al. |
| 2013/0225497 A1 | 8/2013 | Kato et al. |
| 2013/0225501 A1 | 8/2013 | Kato et al. |
| 2013/0310318 A1 | 11/2013 | Ueno et al. |
| 2013/0338336 A1 | 12/2013 | Katoh et al. |
| 2014/0249094 A1 | 9/2014 | Katoh et al. |

FOREIGN PATENT DOCUMENTS

| | | |
|---|---|---|
| JP | 5-32557 | 2/1993 |
| JP | 5-51325 | 3/1993 |
| JP | 2001-346519 | 12/2001 |
| JP | 2004-331564 | 11/2004 |
| JP | 2004-331565 | 11/2004 |
| JP | 2004-331566 | 11/2004 |
| JP | 2005-213260 | 8/2005 |
| JP | 2009-126787 | 6/2009 |
| JP | 2009-126788 | 6/2009 |
| JP | 2009-215301 | 9/2009 |
| JP | 2011-20973 | 2/2011 |
| JP | 2011-519961 | 7/2011 |
| WO | 93/20831 | 10/1993 |
| WO | WO199949840 A1 * | 10/1999 |
| WO | 2009/137880 | 11/2009 |
| WO | 2012/102100 | 8/2012 |

OTHER PUBLICATIONS

International Search Report for International Patent Appl. No. PCT/JP2012/075544, dated Nov. 6, 2012.

International Preliminary Report on Patentability for International Patent Appl. No. PCT/JP2012/075544, dated Apr. 17, 2014.

Extended European Search Report issued in EP Patent Application 12838671.1, dated Jul. 1, 2015.

Tomita et al., J. Dairy Sci. 74: 4137-4142, 1991.

* cited by examiner

SENSATION-IMPROVING AGENT

CROSS-REFERENCE TO RELATED APPLICATIONS

This application is a Divisional of U.S. application Ser. No. 14/349,456, filed Apr. 3, 2014, now abandoned, which is the National Stage of International Application No. PCT/JP2012/075544, filed Oct. 2, 2012, which claims priority to Japanese Patent Application No. 2011-220444, filed Oct. 4, 2011. The disclosure of application Ser. Nos. 14/349,456 and PCT/JP2012/075544 are expressly incorporated by reference herein in their entireties.

TECHNICAL FIELD

The present invention relates to a sensation-improving agent that contains a milk-derived protein and/or a hydrolysate therefrom as an active ingredient, the sensation-improving agent has an effect of improving dulling of peripheral nerves. And the present invention relates to a sensation-improving food, beverage, feed, or cosmetics that includes the sensation-improving agent.

BACKGROUND ART

In recent years, increases in age-related diseases such as osteoporosis and dementia have become a serious social issue associated with aging. Various drugs have been developed to prevent or cure these age-related diseases. However, side effects of such drugs always need to be taken into consideration. Recently, attempts have been made to prevent or cure age-related diseases through a reconsideration of dietary habits or ingestion of a specific food ingredient. For example, ingestion of a basic protein in bovine milk is known to prevent or cure osteoporosis. Furthermore, a preventive and therapeutic agent against Alzheimer's defects of memory, containing sphingomyelin, a relatively abundant phospholipid in bovine milk, as an active ingredient is known.

An example of the age-related symptoms includes dulling of peripheral sensations, which is caused by not only aging, but also diseases such as diabetes. The dulling of peripheral sensations may lead to troubles, for example, a higher risk of suffering burns caused by failure to feel hot rightly on touching a hot object, or a risk of delaying the discovery of an injury caused by a dull sensation of pain. In recent years, studies that reduce dulling of peripheral sensations caused by aging or diseases have been conducted in order to prevent such risks. For example, it has been reported that exogenous ceramide and the enzymes sphingomyelinase and phosphatidylcholine-specific phospholipase C, the enzymes increase biosynthesis of endogenous ceramide, promote morphological differentiation of P-12 cells being neural model cells through 3T3 cells being an established fibroblast cell line, that is, a neurotrophic factor secreted by 3T3 cells (Non Patent Document 1). The promotion of morphological differentiation of the neural model cells indicates the effect of improving dulling of peripheral sensations. However, use of the above ceramide and enzymes, which are not food ingredients, requires examination of their safety. In such situations, there is a need for a safer agent that can improve dulled peripheral sensations through daily ingestion or application to the skin.

Components in milk are known to have many physiological activities. For example, milk-derived sphingomyelin and phospholipids are known to have an effect of improving dulling of peripheral sensations (Patent Document 1 and Patent Document 2). However, the effect of milk-derived proteins on improvements in dulling of peripheral sensations is not yet known. Examples of the milk-derived proteins include lactoperoxidase, lactoferrin, cystatin, and angiogenin.

Lactoperoxidase, present in milk, is a heme iron-containing glycoprotein, while details on its structure are yet to be known. Lactoperoxidase has been found to have an effect of inhibiting in vivo production of lipid peroxides and is used as an anti-aging agent that prevents loss of sight and motor skills, and decline in immune functions and the like, and a liver function improvement agent. Also, the glycoprotein is known to be used as a low-cariogenic nutrient composition due to its low cariogenicity. However, it is yet to be known that lactoperoxidase and an enzymatic hydrolysate therefrom produced with a protease have an effect of improving dulling of peripheral nerves, and are of use as a sensation-improving agent.

Lactoferrin and its hydrolysate are known to have an effect of preventing adhesion of pathogens to cells and an antiviral action. Moreover, the mixture with an epidermal growth factor is reported to increase a skin cell activating effect of the epidermal growth factor alone. Also, lactoferrin is generally known to have an effect of alleviating stress associated with pain and emotional stress. However, it is yet to be known that lactoferrin and an enzymatic hydrolysate therefrom produced with a protease have an effect of improving dulling of peripheral nerves, and are of use as a sensation-improving agent.

Cystatin is a cysteine protease inhibitor that inhibits the proteolytic activity of a cysteine protease having a SH group in the active center, and is found in animal tissues, cells, blood and urine. Also, cystatin's effect of inhibiting virus growth is found to be a beneficial effect. However, it is yet to be known that cystatin and an enzymatic hydrolysate therefrom produced with a protease have an effect of reducing dulling of peripheral nerves, and are of use as a sensation-improving agent.

Angiogenin is one of angiogenesis factors. Human angiogenin is known to be a protein having a molecular weight of 14,400, and is present in blood and milk. Bovine angiogenin is isolated from bovine milk and is subjected to amino acid sequencing, and the results have already been reported. A production of angiogenin from bovine milk by subjecting milk to cation exchange chromatography to apply the milk on the cation exchange column, eluting the adsorbate with an alkali metal salt solution of a weak organic acid, and subjecting the resulting eluate to cation exchange chromatography again and gel filtration chromatography to collect angiogenin is disclosed. Moreover, angiogenin is found to specifically inhibit melanin production in melanoma B-16 cells, and is reported to be used also as a possible whitening agent. However, it is yet to be known that angiogenin and an enzymatic hydrolysate therefrom produced with a protease have an effect of improving dulling of peripheral nerves, and are of use as a sensation-improving agent.

RELATED ART DOCUMENT

Patent Document

Patent Document 1: Japanese Patent Application Laid-Open Publication No. 2009-126787

Patent Document 2: Japanese Patent Application Laid-Open Publication No. 2009-126788

Non Patent Document

Non Patent Document 1: Annual Report of Cosmetology, vol. 10, (2002)
Disclosure of the Invention Problems to be Solved by the Invention

SUMMARY OF THE INVENTION

Problems to be Solved by the Invention

An object of the present invention is to provide a safety sensation-improving agent that can improve dulled peripheral sensations through daily ingestion or application to the skin. Another object of the present invention is to provide a sensation-improving food, beverage, feed, or cosmetics that can improve dulled peripheral sensations through oral ingestion or application to the skin.

Means for Solving the Problems

The present inventors, who have diligently pursued a safe component highly effective for the improvement of dulled sensations in view of these problems, found that oral ingestion or direct application to the skin of any milk-derived protein and/or any hydrolysate therefrom can improve the dulling of sensations, particularly peripheral sensations. Use of such a milk-derived protein and/or a hydrolysate therefrom as an active ingredient has completed a sensation-improving agent. The present inventors also found that the sensation-improving agent can be added with a food, beverage or a feed to form a sensation-improving food, beverage, feed, or cosmetics, and have completed the present invention. Throughout the specification, lactoperoxidase, lactoferrin, cystatin, and angiogenin, which are present in milk, are referred to as "milk-derived proteins". These proteins in use for the sensation-improving agent according to the present invention may not necessarily be derived from milk. For example, they may be synthesized artificially or be purified from blood.

The present invention relates to the following aspects:
(1) A sensation-improving agent containing a milk-derived protein and/or a hydrolysate therefrom as an active ingredient;
(2) The sensation-improving agent according to Aspect (1), wherein the milk-derived protein is at least one selected from lactoperoxidase, lactoferrin, cystatin, and angiogenin;
(3) The sensation-improving agent according to Aspect (1) or (2), wherein the hydrolysate from the milk-derived protein is produced through hydrolisis of the milk-derived protein with a protease;
(4) The sensation-improving agent according to Aspect (3), wherein the protease is at least one selected from the group consisting of pepsin, trypsin, chymotrypsin, and pancreatin;
(5) A sensation-improving food, beverage, feed, or cosmetics containing the component according to any one of Aspects (1) to (4);
(6) A method for improving a sensation in a mammal, including taking the mammal a milk-derived protein and/or a hydrolysate therefrom, or applying the milk-derived protein and/or the hydrolysate therefrom to the skin of the mammal; and
(7) The method according to Aspect (6), wherein the mammal is a human, and the milk-derived protein and/or the hydrolysate therefrom is fed at a dose of 10 mg or more per day for an adult human.

Effect of Invention

The sensation-improving agent according to the present invention can provide an effect of improving dulling of peripheral sensations.

DESCRIPTION OF EMBODIMENTS

The present invention is characterized by a milk-derived protein and/or a hydrolysate therefrom as an active ingredient. Examples of the milk-derived protein include lactoperoxidase, lactoferrin, cystatin, and angiogenin. These milk-derived proteins may be prepared from milk of mammals such as human, cattle, buffalo, goat, and sheep, or be produced by a genetic engineering procedure. Hydrolysates of these milk-derived proteins can be prepared from the milk-derived proteins by the action of a protease.

Lactoperoxidase is prepared from milk of mammals. The examples of the source of milk include mammals such as human, cattle, buffalo, goat, and sheep. Lactoperoxidase, which is a known and commercially available substance, can be industrially produced using known methods, for example, a method for purifying lactoperoxidase with a sulfonated carrier (Japanese Patent Application Laid-Open Publication No. 3-109400). Lactoperoxidase produced by a genetic engineering procedure can also be used in the present invention. A hydrolysate from lactoperoxidase is a peptide mixture prepared by limited proteolysis of the above-described lactoperoxidase with a protease such as trypsin, pancreatin, chymotrypsin, pepsin, papain, kallikrein, cathepsin, thermolysin, or V8 protease so as to have a molecular weight of 10,000 or less. The lower limit of the molecular weight is preferably 500 or more.

Lactoferrin is prepared from milk of mammals. The examples of the source of milk include mammals such as human, cattle, buffalo, goat, and sheep. Lactoferrine, which is a known and commercially available substance, can be industrially produced using known methods, for example, a method for purifying lactoferrin with a sulfonated carrier (Japanese Patent Application Laid-Open Publication No. 3-109400). Lactoferrin produced by a genetic engineering procedure can also be used in the present invention. A hydrolysate from lactoferrin is a peptide mixture prepared by limited proteolysis of the above-described lactoferrin with a protease such as trypsin, pancreatin, chymotrypsin, pepsin, papain, kallikrein, cathepsin, thermolysin, or V8 protease so as to have a molecular weight of 10,000 or less. The lower limit of the molecular weight is preferably 500 or more.

Cystatin from any source can be used, including one derived from milk of mammals such as human, cattle, buffalo, goat, and sheep. For example, the gene sequence of cystatin derived from human milk and bovine milk has already been determined; hence cystatin can be produced by recombinant production, and cystatin produced by a genetic engineering procedure can also be used in the present invention. Alternatively, cystatin, which is relatively abundant in bovine colostrum, may be collected from the milk. Cystatin can also be collected from a cell culture medium, and such cell culture medium-derived cystatin may be used. For example, milk-derived cystatin can be produced in accordance with a known method (Japanese Patent Application Laid-Open Publication No. 2000-281587) from milk such as raw milk, milk powder, skim milk, and reconstituted milk through treatments such as heat treatment, salting treatment, ethanol treatment, various chromatographic treatments such as ion exchange chromatography and gel filtration chromatography, and ultrafiltration treatment. A hydrolysate from cystatin can be a peptide mixture prepared by limited proteolysis of the cystatin with a protease such as trypsin, pancreatin, chymotrypsin, pepsin, papain, kallikrein, cathepsin, thermolysin, or V8 protease so as to have a molecular weight of 8,000 or less. The lower limit of the molecular weight is preferably 500 or more.

For sources of angiogenin, colostrum within 1 to 7 days after parturition, particularly preferably within 1 to 5 days after parturition obtained from mammals such as human, cattle, buffalo, goat, and sheep is suitable because such colostrum has a high angiogenin content, although milk during the original lactation period can also be used as a raw material in the present invention. Angiogenin can be industrially produced using known methods, for example, a method for purifying angiogenin by a combination of cation exchange chromatography and gel filtration chromatography (Japanese Patent Application Laid-Open Publication No. 2-296000). A hydrolysate from angiogenin is a peptide mixture prepared by limited proteolysis of the above-described angiogenin with proteases such as trypsin, pancreatin, chymotrypsin, pepsin, papain, kallikrein, cathepsin, thermolysin, or V8 protease so as to have a molecular weight of 10,000 or less. The lower limit of the molecular weight is preferably 500 or more.

The sensation-improving agent according to the present invention may be used as the above-described milk-derived protein, particularly lactoperoxidase, lactoferrin, cystatin, and angiogenin, or their hydrolysates prepared from the milk-derived protein by the action of a protease, may be mixed with other raw materials, such as saccharides, lipids, proteins, vitamins, minerals, and flavors, commonly used for pharmaceutical products, food and beverage, and feeds, or may be formulated into powders, granules, tablets, capsules, drinks and any other preparation in accordance with conventional methods. The sensation-improving agent according to the present invention can be used as application agent in any conventional application form, such as emulsion, cream, lotion, or pack. These application agents may be produced through conventional methods by appropriately adding a milk-derived protein and/or a hydrolysate therefrom as an active ingredient in the present invention in the course of production, and can also be used as cosmetics. Also, other components that have a sensation-improving effect, for example, ceramide, sphingomyelinase, and sphingomyelin can be used in combination with the milk-derived protein and/or the hydrolysate therefrom. In the test described below for the effective amount of the sensation-improving agent according to the present invention, the milk-derived protein and/or the hydrolysate therefrom was orally ingested in a mouse at a dose of 10 mg or more, preferably 20 mg or more per kg of body weight of the mouse to improve the peripheral sensations in the mouse. The dulling of sensations, particularly peripheral sensations can be expected to be improved by ingesting the milk-derived protein and/or the hydrolysate therefrom typically at a dose of 10 mg or more, preferably 20 mg or more per day for an adult human. It is desirable to ensure the ingestion at this necessary dose. If applied as an application agent to the skin, the density of the applied milk-derived protein and/or hydrolysate therefrom is 0.001 to 40% by weight, more preferably 0.1 to 10% by weight based on the total weight of the application agent.

The sensation-improving food, beverage according to the present invention may be produced by adding the milk-derived protein and/or the hydrolysate therefrom with a conventional food, beverage, for example, yoghurt, a milk beverage, a wafer, and a dessert. Depending on the form of these sensation-improving food, beverage, a milk-derived protein and/or a hydrolysate therefrom is preferably combined in an amount of 0.5 to 2000 mg per 100 g of the food, beverage in order to take a human the milk-derived protein and/or the hydrolysate therefrom at a dose of 10 mg or more per day for an adult human. The sensation-improving feed according to the present invention may be produced by adding the milk-derived protein and/or the hydrolysate therefrom with a conventional feed, for example, a feed for domestic animals and a pet food. For example, if these feeds contain the milk-derived protein and/or the hydrolysate therefrom, a milk-derived protein and/or a hydrolysate therefrom is preferably added in an amount of 0.5 to 2000 mg per 100 g of the feed in order to feed a mammal the milk-derived protein and/or the hydrolysate therefrom at a dose of 10 mg or more.

The milk-derived protein and/or the hydrolysate therefrom may be combined by any method in the present invention. For example, for addition in solution, a milk-derived protein and/or a hydrolysate therefrom is suspended or dissolved in deionized water, and the mixture is stirred followed by formulation of the mixture into the form of a pharmaceutical product, a food, beverage, and a feed. The milk-derived protein and/or the hydrolysate therefrom in deionized water is stirred under such conditions that the milk-derived protein and/or a hydrolysate therefrom may be homogeneously mixed, and can be mixed with an ultradisperser or a TK homomixer. The solution can be concentrated with an RO membrane or freeze-dried, if necessary, to be readily used for a pharmaceutical product, a food, beverage, and a feed. The formulation process in the present invention can include sterilization treatment commonly used in the manufacture of pharmaceutical products, food, beverage, and feeds, and for the formulation in the form of powder, dry-heat sterilization. Accordingly, a pharmaceutical product, a food, beverage, and a feed that contain a milk-derived protein and/or a hydrolysate therefrom according to the present invention can be produced in various forms such as liquid, gel, powder, or granule form.

The present invention will be described below in detail by way of examples and test examples, which are illustrative only and not intended to be limiting the present invention in any way.

Example 1

A column (diameter 5 cm and height 30 cm) filled with 400 g of a cation exchange resin, sulfonated Chitopearl (from Fuji Spinning Co., Ltd.) was thoroughly washed with deionized water, and 40 L of unsterilized skim milk (pH 6.7) was then passed through the column at a flow rate of 25 ml/min. The column was then thoroughly washed with deionized water, and the adsorbate was eluted with a 0.02 M carbonate buffer solution containing 2.0 M sodium chloride (pH 7.0). Eluted fractions containing lactoperoxidase were allowed to apply on an S-Sepharose FF column (from GE Healthcare Ltd.), and the column was thoroughly washed with deionized water, and was equilibrated with a 10 mM phosphate buffer solution (pH 7.0). The adsorbate was then eluted by a linear gradient of 0-2.0 M sodium chloride to collect a fraction containing lactoperoxidase. The fraction was treated by gel filtration chromatography on HiLoad 16/60 Superdex 75 pg (from GE Healthcare Ltd.) to yield 3.0 g of lactoperoxidase. The resulting lactoperoxidase had a purity of 94%, and can be used as a sensation-improving agent (Example Product 1) without further purification.

Example 2

Lactoperoxidase (1 g) prepared in Example 1 was dissolved in 200 ml of water, and a pancreatin (from Sigma Co.) was added to the solution into a final concentration of 0.01% by weight. The solution was treated with the enzyme at 37° C. for 5 hours. The mixture was heat-treated at 90° C. for 5 minutes to deactivate the enzyme, and was freeze-dried to yield 0.8 g of a hydrolysate from lactoperoxidase. The resulting hydrolysate from lactoperoxidase had a molecular weight of 10,000 or less, and can be used as a sensation-improving agent (Example Product 2) without further purification.

Example 3

Lactoperoxidase (1 g) prepared in Example 1 was dissolved in 200 ml of water, and a trypsin (from Sigma Co.) was added to the solution into a final concentration of 0.01% by weight. The solution was treated with the enzyme at 37° C. for 5 hours. The mixture was heat-treated at 90° C. for 5 minutes to deactivate the enzyme, and was freeze-dried to yield 0.9 g of a hydrolysate from lactoperoxidase. The resulting hydrolysate from lactoperoxidase had a molecular weight of 10,000 or less, and can be used as a sensation-improving agent (Example Product 3) without further purification.

Example 4

A column (diameter 5 cm and height 30 cm) filled with 400 g of a cation exchange resin sulfonated Chitopearl (from Fuji Spinning Co., Ltd.) was thoroughly washed with deionized water, and 40 L of unsterilized skim milk (pH 6.7) was then passed through the column at a flow rate of 25 ml/min. The column was then thoroughly washed with deionized water, and the adsorbate was eluted with a 0.02 M carbonate buffer solution containing 2.0 M sodium chloride (pH 7.0). Eluted fractions containing lactoferrin were allowed to apply on an S-Sepharose FF column (from GE Healthcare Ltd.), and the column was thoroughly washed with deionized water, and was equilibrated with a 10 mM phosphate buffer solution (pH 7.0). The adsorbate was then eluted by a linear gradient of 0-2.0 M sodium chloride to collect a fraction containing lactoferrin. The fraction was treated by gel filtration chromatography on HiLoad 16/60 Superdex 75 pg (from GE Healthcare Ltd.) to yield 8.0 g of lactoferrin. The resulting lactoferrin had a purity of 96%, and can be used as a sensation-improving agent (Example Product 4) without further purification.

Example 5

Lactoferrin (1 g) prepared in Example 4 was dissolved in 200 ml of water, and a pancreatin (from Sigma Co.) was added to the solution into a final concentration of 0.01% by weight. The solution was treated with the protease at 37° C. for 5 hours. The mixture was heat-treated at 90° C. for 5 minutes to deactivate the enzyme, and was freeze-dried to yield 0.8 g of a hydrolysate from lactoferrin. The resulting hydrolysate from lactoferrin had a molecular weight of 10,000 or less, and can be used as a sensation-improving agent (Example Product 5) without further purification.

Example 6

Lactoferrin (1 g) prepared in Example 4 was dissolved in 200 ml of water, and a trypsin (from Sigma Co.) was added to the solution into a final concentration of 0.01% by weight. The solution was treated with the protease at 37° C. for 5 hours. The mixture was heat-treated at 90° C. for 5 minutes to deactivate the enzyme, and was freeze-dried to yield 0.9 g of a hydrolysate from lactoferrin. The resulting hydrolysate from lactoferrin had a molecular weight of 10,000 or less, and can be used as a sensation-improving agent (Example Product 6) without further purification.

Example 7

A column filled with 3,000 g of S-Sepharose was thoroughly washed with deionized water, and 10,000 L of skim milk was then passed through the column. The column was thoroughly washed with deionized water, and the adsorbate was then eluted by a linear concentration gradient with 0.1 to 1.0 M sodium chloride. The resulting fractions were heat-treated at 90° C. for 10 minutes and were then centrifuged to remove precipitates. The eluted fraction containing bovine milk-derived basic cystatin was again fractionated by Mono S ion exchange chromatography. This fraction was treated sequentially by Mono Q ion exchange chromatography and Superose 12 gel filtration chromatography in an FPLC system, and subsequently hydroxyapatite chromatography and C4 reverse phase chromatography in an HPLC system to yield 58 mg of cystatin (Fraction A). The resulting cystatin can be used as a sensation-improving agent (Example Product 7) without further purification.

Example 8

A 5% whey protein solution (10,000 L) was heat-treated at 90° C. for 10 minutes, and was then centrifuged to remove precipitates. A column was filled with a carrier prepared by binding carboxymethylated papain to Tresyl-Toyopearl (from TOSOH CORPORATION), and was then equilibrated with a 0.5 M sodium chloride solution. The above-described whey protein solution was passed through the column. The column was washed with a 0.5 M sodium chloride solution and then a 0.5 M sodium chloride solution containing 0.1% Tween 20. Cysteine protease was then eluted with a 20 mM acetic acid-0.5 M sodium chloride solution. Eluted fractions were immediately neutralized with a 1 M sodium hydroxide solution. The neutralized solution was fractionated by Mono S anion exchange chromatography, hydroxyapatite chromatography, and then C4 reverse phase chromatography in an HPLC system to yield 48 mg of milk-derived basic cystatin (Fraction B). The resulting cystatin can be used as a sensation-improving agent (Example Product 8) without further purification.

Example 9

Fraction A (25 mg) prepared in Example 7 was suspended in 100 ml of water, and pancreatin was added to the suspension into a final concentration of 1% by weight. The suspension was treated with the enzyme at 37° C. for 5 hours. The suspension was heat-treated at 90° C. for 5 minutes to deactivate the enzyme, and was freeze-dried to yield 23 mg of a hydrolysate from cystatin (Fraction C). The fraction B (25 mg) prepared in Example 8 was treated in a similar manner to yield 24 mg of a hydrolysate from cystatin (Fraction D). The resulting hydrolysate from cystatin had a molecular weight of 8,000 or less, and can be used as a sensation-improving agent (Example Product 9) without further purification.

Example 10

A column (diameter 5 cm and height 30 cm) filled with 400 g of a cation exchange resin sulfonated Chitopearl (from Fuji Spinning Co., Ltd.) was thoroughly washed with deionized water, and 40 L of unsterilized skim milk (pH 6.7) was then passed through the column at a flow rate of 25 ml/min. The column was then thoroughly washed with deionized water, and the adsorbate was eluted with a 0.02 M carbonate buffer solution containing 2.0 M sodium chloride (pH 7.0). Eluted fractions containing angiogenin were allowed to apply on an S-Sepharose FF column (from GE Healthcare Ltd.), and the column was thoroughly washed with deionized water, and was equilibrated with a 10 mM phosphate buffer solution (pH 7.0). The adsorbate was then eluted by a linear gradient of 0-2.0 M sodium chloride to collect a fraction containing angiogenin. The fraction was treated by gel filtration chromatography on HiLoad 16/60 Superdex 75 pg (from GE Healthcare Ltd.) to yield 1.8 g of a fraction abundantly containing angiogenin. The angiogenin content in the resulting fraction abundantly containing angiogenin is 10%, and the fraction can be used as a sensation-improving agent (Example Product 10).

Example 11

A column filled with 3,000 g of a cation exchange resin, sulfonated Chitopearl (from Fuji Spinning Co., Ltd.) was thoroughly washed with deionized water, and 100 L of unsterilized skim milk (pH 6.7) was then passed through the column. This column was then thoroughly washed with deionized water, and the adsorbate was eluted by a linear concentration gradient of 0.1 to 2.0 M sodium chloride. The eluted fraction containing angiogenin was fractionated by S-Sepharose cation exchange chromatography (from GE Healthcare Ltd.), the resulting fraction containing angiogenin was heat-treated at 90° C. for 10 minutes, and was centrifuged to remove precipitates. This fraction containing angiogenin was sequentially treated by Mono S cation exchange chromatography, Superose 12 gel filtration chromatography, hydroxyapatite chromatography, and C4 reverse phase chromatography to yield 55 mg of angiogenin. The resulting angiogenin had a purity of 99%, and can be used as a sensation-improving agent (Example Product 11).

Example 12

Angiogenin (5 mg) prepared in Example 11 was dissolved in 10 ml of water, and pancreatin (from Sigma Co.) was added to the solution into a final concentration of 0.01% by weight. The solution was treated with the enzyme at 37° C. for 5 hours. The solution was heat-treated at 90° C. for 5 minutes to deactivate the enzyme, and was freeze-dried to yield 4.0 mg of a hydrolysate from angiogenin. The resulting hydrolysate from angiogenin had a molecular weight of 10,000 or less, and can be used as a sensation-improving agent (Example Product 12) without further purification.

Example 13

Angiogenin (5 mg) prepared in Example 11 was dissolved in 10 ml of water, and trypsin (from Sigma Co.) was added to the solution into a final concentration of 0.01% by weight. The solution was treated with the enzyme at 37° C. for 5 hours. The solution was heat-treated at 90° C. for 5 minutes to deactivate the enzyme, and was freeze-dried to yield 4.2 mg of a hydrolysate from angiogenin. The resulting hydrolysate from angiogenin had a molecular weight of 10,000 or less, and can be used as a sensation-improving agent (Example Product 13) without further purification.

Test Example 1

(Verification of Promotion of Cell Differentiation)

3T3 cells being a fibroblast cell line that is known to be present in the skin were incubated for two days in the presence of Example Products 1, 3, 4, 5, and 7, Fraction C in Example Product 9, and Example Products 11 and 13, each in a concentration of 0.03 to 1%. As a control, 3T3 cells were incubated for two days in the absence of any Example Product (control). PC-12 cells being neural model cells were incubated with those culture supernatants, and morphological differentiation of the PC-12 cells was observed when a neurotrophic factor was secreted by 3T3 cells.

The results showed that all of the culture supernatants containing an Example Product differentiated PC-12 cells clearly. This experiment was repeated several times, and the proportion of differentiation was observed with an optical microscope. When any Example Product was added, differentiation was observed in 95% or more of the cells. In contrast, the control culture supernatant failed to differentiate PC-12 cells, and observation with an optical microscope in the experiment that was repeated several times revealed no differentiation. This shows that a milk-derived protein and/or a hydrolysate therefrom promotes the secretion of a neurotrophic factor from 3T3 cells, and promotes the differentiation of PC-12 cells being neural model cells.

Test Example 2

(Verification of Sensation-Improving Effect in Animal Experiments)

A sensation-improving effect by thermal stimulation was evaluated in the hot plate that is a behavioral study to thermal stimulation developed by Woolfe, MacDonald, et al. 24-weeks old hairless mice (Hos:HR-1) were divided into 13 groups with 6 mice in each group. Example Products 2, 6, and 8, Fraction D in Example Product 9, Example Products 10 and 12 were each orally administered to a mouse through a sonde in a dose of 10 mg or 20 mg once daily per kg body weight in a mouse, or a vehicle only was orally administered to a mouse through a tube once daily (control; 0 mg), and these mice were bred for 4 weeks. At the end of the administration, mice were placed on a hot plate at 54° C., and the time until the mice exhibited escape behavior, such as pulling their paws away from the hot plate, standing up, and jumping was measured. The maximal strength of thermal stimulation was set to 30 seconds, the value at this maximal strength was assigned to 30 seconds. The results are shown in Table 1.

TABLE 1

| | | escape behavior positive response time |
|---|---|---|
| control | 0 mg | 29.2 ± 0.14 seconds |
| Example Product 2 | 10 mg | 22.2 ± 0.17 seconds |
| | 20 mg | 20.1 ± 0.25 seconds |
| Example Product 6 | 10 mg | 22.8 ± 0.18 seconds |
| | 20 mg | 20.5 ± 0.22 seconds |
| Example Product 8 | 10 mg | 23.1 ± 0.27 seconds |
| | 20 mg | 21.0 ± 0.13 seconds |
| Example Product 9 | 10 mg | 23.3 ± 0.10 seconds |
| (Fraction D) | 20 mg | 21.1 ± 0.21 seconds |
| Example Product 10 | 10 mg | 26.2 ± 0.17 seconds |
| | 20 mg | 24.1 ± 0.16 seconds |
| Example Product 12 | 10 mg | 23.9 ± 0.21 seconds |
| | 20 mg | 21.8 ± 0.20 seconds |

Table 1 demonstrates that ingestion of Example Products 2, 6, and 8, Fraction D in Example Product 9, and Example Products 10 and 12 each show a tendency toward a shorter escape behavior positive response time at a dose of 10 mg, and significantly shortened the time at a dose of 20 mg. This indicates that ingestion of Example Products 2, 6, and 8, Fraction D in Example Product 9, and Example Products 10 and 12 can prevent or improve the dulling of sensations, particularly peripheral sensations.

Test Example 3

(Verification of Sensation-Improving Effect by Oral Ingestion)

Healthy elderly subjects (average age 75±3) who experienced dulled sensations in the hand were divided into 9 groups with 10 subjects in each group. These groups consisted of Group A with ingestion of no Example Product, Group B with ingestion of Example Product 1 at a dose of 10 mg, Group C with ingestion of Example Product 1 at a dose of 20 mg, Group D with ingestion of Example Product 4 at a dose of 10 mg, Group E with ingestion of Example Product 4 at a dose of 20 mg, Group F with ingestion of Example Product 7 at a dose of 10 mg, Group G with ingestion of Example Product 7 at a dose of 20 mg, Group H with ingestion of Example Product 11 at a dose of 10 mg, and Group I with ingestion of Example Product 11 at a dose of 20 mg, and such ingestion was continued for 6 weeks. As determined with an algesiometer (from Intercross) which is an instrument for determining superficial sensations in accordance with the manufacturer's directions for use before and after the 6-week ingestion, pain sensations in the palm of the hand and the sole of the foot were graded in four ranks from normal to declines I to III on the basis of pain sensations in the medial side of the arm. The results are shown in Tables 2 and 3. Moreover, after the 6-week ingestion, a questionnaire survey was conducted to each subject on the improvement of his/her sensation in the hand. The results are shown in Tables 4 and 5.

(Measurement)

The pain sensation was evaluated using five pins that have different thicknesses in combination with five positions of a fulcrum. The thinnest pin 1 was rolled along the medial side of the arm, and the subject was asked about the degree of normal pain sensation. The pin 1 was then rolled along the palm and the sole of the foot while the position of the fulcrum for the holder was sequentially changed to determine the position of the fulcrum at which the same degree of pain sensation as the first pain sensation was caused.

(Evaluation)

The algesiometer was designed to cause pain sensations in the same degree in rolling the pin 1 (fulcrum: 50 g) along the medial side of the arm and in rolling the pin 2 (fulcrum: 50 g) along the palm, and was used in accordance with the manufacturer's directions for use to evaluate the pain sensation as described below. The evaluation of the pain was scored and the scores were averaged.

Normal (score 0): The pain sensation in the same degree was caused in rolling the pin 2 (50 g)

Decline I (score 1): The pain sensation in the same degree was caused in rolling the pin 1 (50 g)

Decline II (score 2): The pain sensation in the same degree was caused in rolling the pin 1 (60 g)

Decline III (score 3): The pain sensation in the same degree was caused in rolling the pin 1 (70 g)

| | Normal | Decline I | Decline II | Decline III | Average value |
|---|---|---|---|---|---|
| Measurement of sensation in the hand (Before ingestion) | | | | | |
| Group A | 0 | 2 | 3 | 5 | 2.3 |
| Group B | 0 | 1 | 5 | 4 | 2.3 |
| Group C | 0 | 1 | 5 | 4 | 2.3 |
| Group D | 0 | 1 | 4 | 5 | 2.4 |
| Group E | 0 | 1 | 5 | 4 | 2.3 |
| Group F | 0 | 2 | 3 | 5 | 2.3 |
| Group G | 0 | 1 | 5 | 4 | 2.3 |
| Group H | 0 | 1 | 5 | 4 | 2.3 |
| Group I | 0 | 1 | 4 | 5 | 2.4 |
| Measurement of sensation in the hand (After 6-week ingestion) | | | | | |
| Group A | 0 | 2 | 4 | 4 | 2.2 |
| Group B | 0 | 3 | 5 | 2 | 1.9 |
| Group C | 2 | 4 | 3 | 1 | 1.3 |
| Group D | 1 | 2 | 4 | 3 | 1.9 |
| Group E | 2 | 2 | 5 | 1 | 1.5 |
| Group F | 0 | 3 | 5 | 2 | 1.9 |
| Group G | 2 | 4 | 3 | 1 | 1.3 |
| Group H | 1 | 2 | 4 | 3 | 1.9 |
| Group I | 2 | 2 | 5 | 1 | 1.5 |

TABLE 3

| | Normal | Decline I | Decline II | Decline III | Average value |
|---|---|---|---|---|---|
| Measurement of sensation in the sole of the foot (Before ingestion) | | | | | |
| Group A | 0 | 2 | 3 | 5 | 2.3 |
| Group B | 0 | 1 | 4 | 5 | 2.4 |
| Group C | 0 | 1 | 3 | 6 | 2.5 |
| Group D | 0 | 1 | 6 | 3 | 2.2 |
| Group E | 0 | 1 | 4 | 5 | 2.4 |
| Group F | 0 | 2 | 3 | 5 | 2.3 |
| Group G | 0 | 1 | 4 | 5 | 2.4 |
| Group H | 0 | 1 | 3 | 6 | 2.5 |
| Group I | 0 | 1 | 6 | 3 | 2.2 |
| Measurement of sensation in the sole of the foot (After 6-week ingestion) | | | | | |
| Group A | 0 | 2 | 3 | 5 | 2.3 |
| Group B | 1 | 4 | 1 | 4 | 1.8 |
| Group C | 2 | 3 | 3 | 2 | 1.5 |
| Group D | 0 | 3 | 6 | 1 | 1.8 |
| Group E | 1 | 3 | 5 | 1 | 1.6 |
| Group F | 1 | 4 | 1 | 4 | 1.8 |
| Group G | 2 | 3 | 3 | 2 | 1.5 |
| Group H | 0 | 3 | 6 | 1 | 1.8 |
| Group I | 1 | 3 | 5 | 1 | 1.6 |

TABLE 4

Sensation in the hand

| | Deteriorated | Unchanged | Recovered |
|---|---|---|---|
| Group A | 2 | 7 | 1 |
| Group B | 1 | 5 | 4 |
| Group C | 0 | 2 | 8 |
| Group D | 0 | 3 | 7 |
| Group E | 0 | 2 | 8 |
| Group F | 1 | 5 | 4 |
| Group G | 0 | 2 | 8 |
| Group H | 0 | 3 | 7 |
| Group I | 0 | 2 | 8 |

TABLE 5

Sensation in the sole of the foot

| | Deteriorated | Unchanged | Recovered |
|---|---|---|---|
| Group A | 2 | 7 | 1 |
| Group B | 0 | 6 | 4 |
| Group C | 0 | 2 | 8 |
| Group D | 0 | 5 | 5 |
| Group E | 0 | 2 | 8 |
| Group F | 0 | 6 | 4 |
| Group G | 0 | 2 | 8 |
| Group H | 0 | 5 | 5 |
| Group I | 0 | 2 | 8 |

Tables 2 to 5 demonstrate that ingestion of Example Products 1, 4, 7, and Example Product 11 each show a tendency toward improved sensations in the hand and the sole of the foot at a dose of 10 mg, and significantly improved the sensations at a dose of 20 mg. The dulled sensations, particularly peripheral sensations can be expected to be improved by ingesting the milk-derived protein and/or the hydrolysate therefrom typically at a dose of 10 mg or more, preferably 20 mg or more per day for an adult human.

Example 14

(Preparation of Sensation-Improving Cosmetic Product (Cream))

A hydrolysate from lactoperoxidase prepared in Example 3 (Example Product 3) was used to produce a sensation-improving cosmetic product (cream) by mixing with raw materials in the proportion shown in Table 6.

TABLE 6

Line 6: Hydrolysate from lactoperoxidase

| | |
|---|---|
| Glyceryl monostearate (self-emulsifiable) | 10.0 |
| Purified lanolin | 6.0 |
| Liquid paraffin | 5.0 |
| Jojoba oil | 5.0 |
| Paraben | 0.3 |
| Decomposed product from lactoperoxidase (Example Product 3) | 1.0 |
| Flavoring agent | Appropriate amount |
| Sterile ion exchanged water | q.s to 100.0 |

Test Example 4

(Test for Sensation-Improving Effect by Application to the Skin)

Healthy elderly subjects (average age 75±3) who experienced dulled sensations in the hand were divided into 2 groups, Group A and Group B with 15 subjects in each group. A cosmetic product (cream) prepared as in Example Product 14 except that any sensation-improving agent was not contained was applied to subjects in Group A, and a sensation-improving cosmetic product (cream) in Example Product 14 to subjects in Group B once daily over their hands and feet. The application was continued for 6 weeks. As determined with an algesiometer (from Intercross) which is an instrument for determining superficial sensations in accordance with the manufacturer's directions for use before and after the 6-week application, pain sensations in the palm of the hand and the sole of the foot were graded in four ranks from normal to declines I to III on the basis of pain sensations in the medial side of the arm. The results are shown in Tables 7 and 8. Moreover, after the 6-week application, a questionnaire survey was conducted to each subject on the improvement of his/her sensation in the hand. The results are shown in Tables 9 and 10. The measurement was carried out as in Test example 3.

TABLE 7

| | Normal | Decline I | Decline II | Decline III | Average value |
|---|---|---|---|---|---|
| Measurement of sensation in the hand (Before application) | | | | | |
| Group A | 0 | 4 | 6 | 5 | 2.1 |
| Group B | 0 | 5 | 4 | 6 | 2.1 |
| Measurement of sensation in the hand (After 6-week application) | | | | | |
| Group A | 1 | 3 | 7 | 4 | 1.9 |
| Group B | 3 | 6 | 3 | 3 | 1.4 |

TABLE 8

| | Normal | Decline I | Decline II | Decline III | Average value |
|---|---|---|---|---|---|
| Measurement of sensation in the sole of the foot (Before application) | | | | | |
| Group A | 0 | 5 | 5 | 5 | 2.0 |
| Group B | 0 | 5 | 6 | 4 | 1.9 |
| Measurement of sensation in the sole of the foot (After 6-week application) | | | | | |
| Group A | 1 | 3 | 5 | 6 | 2.1 |
| Group B | 2 | 6 | 6 | 1 | 1.4 |

TABLE 9

Sensation in the hand

| | Deteriorated | Unchanged | Recovered |
|---|---|---|---|
| Group A | 2 | 12 | 1 |
| Group B | 1 | 6 | 8 |

TABLE 10

Sensation in the sole of the foot

| | Deteriorated | Unchanged | Recovered |
|---|---|---|---|
| Group A | 1 | 13 | 1 |
| Group B | 0 | 9 | 6 |

Tables 7 to 10 demonstrate that application of the sensation-improving cosmetic product (cream) in Example Product 14 shows a tendency toward improved sensations in the hand and the sole of the foot. This indicates that the dulled peripheral sensations can be expected to be improved by applying the cream containing a sensation-improving agent according to the present invention.

Example 15

(Preparation of Sensation-Improving Liquid Nutrient Composition)

A hydrolysate (5 g) from lactoferrin in Example Product 5 was dissolved in 4995 g of deionized water, the solution was stirred with a TK homomixer (TKROBO MICS; from Tokusyukika) at 6000 rpm for 30 minutes to prepare a solution of the hydrolysate from lactoferrin having a content of the hydrolysate from lactoferrin of 100 mg/100 g. To 5.0 kg of the solution of the hydrolysate from lactoferrin were added 4.0 kg of casein, 5.0 kg of soy protein, 1.0 kg of fish oil, 3.0 kg of perilla oil, 18.0 kg of dextrin, 6.0 kg of a mineral mixture, 1.95 kg of a vitamin mixture, an 2.0 kg of emulsifier, 4.0 kg of stabilizer, and 0.05 kg of a flavoring agent. The mixture was then placed into a 200 ml retort pouch. The retort pouch was sterilized with a retort sterilizer (Class-1 pressure vessel, TYPE: RCS-4CRTGN, from HISAKA WORKS, LTD.) at 121° C. for 20 minutes to prepare 50 kg of a sensation-improving liquid nutrient composition according to the present invention. The resulting sensation-improving liquid nutrient composition had no precipitate, nor any abnormality of taste. The sensation-improving liquid nutrient composition had a content of the hydrolysate from lactoferrin of 10 mg/100 g.

Example 16

(Preparation of Sensation-Improving Gel Food)

Cystatin (2 g) in Example Product 8 was dissolved in 708 g of deionized water, and the solution was stirred with an ultra-disperser (ULTRA-TURRAXT-25; from IKA Japan) at 9500 rpm for 30 minutes. To the solution were added 40 g of sorbitol, 2 g of an acidulant, 2 g of a flavoring agent, 5 g of pectin, 5 g of a whey protein concentrate, 1 g of calcium lactate, and 235 g of deionized water. The mixture was stirred and was placed into a 200 ml cheer pack. The cheer pack was sterilized at 85° C. for 20 minutes, and was then sealed to prepare 5 bags (each 200 g) of a sensation-improving gel food according to the present invention. The resulting sensation-improving gel food had no precipitate, nor any abnormality of taste. The sensation-improving gel food had a cystatin content of 200 mg/100 g.

Example 17

(Preparation of Sensation-Improving Beverage)

An acidulant (2 g) was dissolved in 706 g of deionized water, and 4 g of angiogenin in Example Product 11 was then dissolved in the solution. The mixture was stirred with an ultra-disperser (ULTRA-TURRAXT-25; from IKA Japan) at 9500 rpm for 30 minutes. To the mixture were added 100 g of maltitol, 20 g of a reduced starch syrup, 2 g of a flavoring agent, and 166 g of deionized water, and the mixture was filled into a 100 ml glass bottle. The bottle was sterilized at 95° C. for 15 seconds and was sealed to prepare 10 bottles (each 100 ml) of a sensation-improving beverage. The resulting sensation-improving beverage had no precipitate, nor any abnormality of taste. The sensation-improving beverage had an angiogenin content of 400 mg/100 g.

Example 18

(Preparation of Sensation-Improving Feed)

A hydrolysate from lactoperoxidase (2 kg) in Example Product 2 was dissolved in 98 kg of deionized water, and the solution was stirred with a TK homomixer (MARK II Model 160; from Tokusyukika) at 3600 rpm for 40 minutes to prepare a solution of a hydrolysate from lactoperoxidase having a content of the hydrolysate from lactoperoxidase of 2 g/100 g. To 10 kg of the solution of the hydrolysate from lactoperoxidase were added 12 kg of soybean cake, 14 kg of skim milk powder, 4 kg of soybean oil, 2 kg of corn oil, 23.2 kg of palm oil, 14 kg of corn starch, 9 kg of wheat flour, 2 kg of bran, 5 kg of a vitamin mixture, 2.8 kg of cellulose, and 2 kg of a mineral mixture, and the mixture was sterilized at 120° C. for 4 minutes to prepare 100 kg of a sensation-improving canine feed according to the present invention. The sensation-improving canine feed had a content of the hydrolysate from lactoperoxidase of 200 mg/100 g.

Example 19

(Preparation of Sensation-Improving Agent (Tablet))

The raw materials were mixed in the proportion shown in Table 11, and the mixture was shaped into 1-g tablets in accordance with a conventional method to prepare a sensation-improving agent according to the present invention. The sensation-improving agent had a lactoperoxidase content of 100 mg/g.

TABLE 11

| Hydrous crystalline glucose | 83.5% (% by weight) |
|---|---|
| Lactoperoxidase (Example Product 1) | 10.0% |
| Mineral mixture | 5.0% |
| Sugar ester | 1.0% |
| Flavoring agent | 0.5% |

Example 20

(Preparation of Sensation-Improving Cosmetic Product (Lotion))

The raw materials were mixed in the proportion shown in Table 12 to prepare a sensation-improving cosmetic product (lotion).

TABLE 12

| Sorbitol | 3.0 |
|---|---|
| Sodium DL-pyrrolidone carboxylate | 2.0 |
| Carboxymethyl cellulose | 0.3 |
| Paraben | 0.1 |
| Lactoferrin (Example Product 4) | 1.5 |
| Flavoring agent | Appropriate amount |
| Sterile ion exchanged water | q.s to 100.0 |

What is claimed is:

1. A method for improving dulled peripheral sensation in a mammal, comprising:
    orally administering a milk-derived protein and/or a hydrolysate therefrom to a mammal with dulled peripheral sensation at a dose of 10 mg or more per day; or
    administering a milk-derived protein and/or a hydrolysate therefrom to the skin of a mammal with dulled peripheral sensation;

wherein said milk-derived protein comprises lactoperoxidase
thereby improving dulled peripheral sensation in said mammal.

2. The method of claim 1, wherein said mammal is a human, and said milk-derived protein and/or hydrolysate therefrom is orally administered at a dose of 10 mg or more per day for an adult human.

3. The method of claim 2, wherein said milk-derived protein and/or hydrolysate therefrom is orally administered at a dose of 10-20 mg per day for an adult human.

4. The method of claim 1, further comprising contacting said milk-derived protein with a protease to produce said hydrolysate.

5. The method of claim 4, wherein said protease comprises pepsin, trypsin, chymotrypsin, or pancreatin.

6. The method of claim 1, comprising orally administering a food, beverage, or feed comprising said milk-derived protein and/or said hydrolysate therefrom to said mammal.

7. The method of claim 1, comprising applying a cosmetic containing said milk-derived protein and/or said hydrolysate therefrom to the skin of said mammal.

8. The method of claim 7, wherein the density of said applied milk-derived protein and/or said hydrolysate therefrom is 0.001 to 40% by weight of said cosmetic.

9. The method of claim 8, wherein the density of said applied milk-derived protein and/or said hydrolysate therefrom is 0.1 to 10% by weight of said cosmetic.

10. A method for improving dulled peripheral sensation in a mammal, comprising orally administering to a mammal with dulled peripheral sensation a purified milk-derived protein and/or a hydrolysate therefrom, wherein said milk-derived protein comprises lactoperoxidase thereby improving dulled peripheral sensation in said mammal.

11. The method of claim 10, wherein said mammal is a human, and said milk-derived protein and/or hydrolysate therefrom is orally administered at a dose of 10 mg or more per day for an adult human.

12. The method of claim 11, wherein said milk-derived protein and/or hydrolysate therefrom is orally administered at a dose of 10-20 mg per day for an adult human.

13. A method for improving dulled peripheral sensation in a mammal comprising administering to a mammal with dulled peripheral sensation a hydrolysate of at least one milk-derived protein orally or to the skin of said mammal, wherein the milk-derived protein comprises lactoperoxidase, thereby improving dulled peripheral sensation.

14. The method of claim 13, further comprising contacting said milk-derived protein with a protease to produce said hydrolysate.

15. The method of claim 14, wherein said protease comprises pepsin, trypsin, chymotrypsin, or pancreatin.

16. The method of claim 13, wherein said hydrolysate has a molecular weight of 10,000 Da or less.

17. The method of claim 13, wherein said hydrolysate has a molecular weight of 8,000 Da or less.

18. The method of claim 13, wherein said hydrolysate has a molecular weight of 500 Da and 10,000 Da.

19. The method of claim 1, wherein said milk-derived protein and/or hydrolysate therefrom is orally administered at a dose of 10-20 mg per day for an adult human.

* * * * *